United States Patent
Sebillotte-Arnaud et al.

(10) Patent No.: US 7,670,999 B2
(45) Date of Patent: Mar. 2, 2010

(54) CLEANSING COMPOSITION CONTAINING HYDROPHILIC SILICA AND OXYALKENYLATED COMPOUNDS

(75) Inventors: Laurence Sebillotte-Arnaud, L'Hay les Roses (FR); Veronique Guillou, Antony (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/903,785

(22) Filed: Jul. 13, 2001

(65) Prior Publication Data

US 2002/0035047 A1 Mar. 21, 2002

(30) Foreign Application Priority Data

Jul. 13, 2000 (FR) .................................. 00 09225

(51) Int. Cl.
*A61K 7/50* (2006.01)
(52) U.S. Cl. .................. 510/130; 510/156; 510/505; 424/70.1
(58) Field of Classification Search ................. 510/130, 510/136, 156, 466, 505, 506; 424/70
See application file for complete search history.

(56) References Cited

U.S. PATENT DOCUMENTS

| | | | |
|---|---|---|---|
| 4,450,090 A | 5/1984 | Kinney | |
| 5,055,229 A | 10/1991 | Pelton et al. | |
| 5,512,277 A | 4/1996 | Uemura et al. | |
| 5,783,536 A | 7/1998 | Farrell et al. | |
| 5,824,296 A | 10/1998 | Dubief et al. | |
| 5,867,238 A | 2/1999 | Miller et al. | |
| 5,972,859 A | 10/1999 | Farrell et al. | |
| 6,063,368 A | 5/2000 | Kapsner et al. | |
| 6,093,769 A | 7/2000 | Burdick et al. | |
| 6,277,797 B1 * | 8/2001 | Glenn, Jr. et al. | ........... 510/130 |
| 2002/0039976 A1 | 4/2002 | Sebillotte-Arnaud et al. | |

FOREIGN PATENT DOCUMENTS

| | | |
|---|---|---|
| EP | 0 288 419 | 10/1988 |
| EP | 0 514 760 A1 | 11/1992 |
| EP | 0 692 248 A1 | 1/1996 |
| EP | 1 172 095 | 1/2002 |
| JP | 61-180712 | 8/1986 |
| WO | WO 93/08793 | 5/1993 |
| WO | WO 96/28140 | 9/1996 |
| WO | WO 97/49381 | 12/1997 |
| WO | WO 99/25313 | 5/1999 |
| WO | WO 99/38488 | 8/1999 |
| WO | WO 00/38621 | 7/2000 |

OTHER PUBLICATIONS

Chemical Abstracts, AN 1987:38232, JP 61 180712, Aug. 13, 1986. XP-002168472.
Chemical Abstracts, AN 1992-180847, JP 04 120015, Apr. 21, 1992. XP-002168473.
T. Someya et al, Database Caplus, XP-002168470, AN 1987:38232, JP 61180712, "Stable cleansing creams".
Database WPI, Week 199222, XP-002168471, AN 1992-180847, JP 04120015, Derwent Publications Ltd., London, GB.

* cited by examiner

*Primary Examiner*—Necholus Ogden, Jr.
(74) *Attorney, Agent, or Firm*—Oblon, Spivak, McClelland, Maier & Neustadt, L.L.P.

(57) ABSTRACT

A cleansing composition comprising (1) at least one foaming surfactant, (2) at least 1% by weight of at least one hydrophilic silica, relative to the total weight of the composition, and (3) at least one oxyalkylenated compound in a physiologically acceptable aqueous medium comprising at least 35% by weight of water, relative to the total weight of the composition.

23 Claims, No Drawings

CLEANSING COMPOSITION CONTAINING HYDROPHILIC SILICA AND OXYALKENYLATED COMPOUNDS

BACKGROUND OF THE INVENTION

1. Field of the Invention

The present invention relates to a rinsable foaming cleansing composition containing at least one hydrophilic silica and at least one oxyalkylenated compound, and to the use of the said composition in particular in cosmetics as cleansing products or makeup-removing products for the skin, the eyes, the scalp and/or the hair, and also for treating greasy skin and/or for disinfecting the skin and/or the scalp.

2. Discussion Of The Background

Cleansing the skin is very important for the care of the face. Cleansing must be as efficient as possible because greasy residues, such as excess sebum, the remnants of cosmetic products used daily and make-up products accumulate in the folds of the skin and can block the pores of the skin and result in the appearance of spots.

One means of cleansing the skin properly is to use foaming cleansing products. The foaming cleansing products that are currently commercially available are in the form of foaming bars, gels or creams, and they may or may not contain soaps (fatty acid salts). Soap-containing foaming products have the advantage of giving a creamy lather; however, certain consumers find fault with these products because they cause tautness of the skin because of their excessive detergency. Thus, efforts have been made to formulate products which are better tolerated by the skin, by reducing the soap content. However, the product then has an insufficient viscosity.

Moreover, soap-free foaming products are generally well tolerated by the skin. However, they are generally in the form of liquid products or relatively fluid gels. In order to thicken soap-free foaming products, a known practice has been to add thickeners thereto such as alkyl- or acyl-oxyethylenated compounds, polysaccharides such as cellulose derivatives, guar gums and its derivatives, and acrylic polymers. However, in order to increase the viscosity of a soap-free foaming product and to obtain a thick texture, it is necessary to introduce large amounts of these thickeners into the soap-free formulations. Now, when the percentage of alkyl- or acyloxyethylenated compounds, such as oxyethylenated alkylglucose esters such as, for example, PEG-120 methylglucose dioleate or ceteareth-60 myristyl glycol, which are conventionally used, is increased, a formulation is obtained which is not homogeneous and which does not spread uniformly on the skin because it spreads in blobs, which renders these compositions unacceptable to the user. In addition, it is then difficult for lather to develop. Furthermore, it is not possible to increase the percentage of these thickeners indefinitely, because they reach a solubility limit in the medium of the preparation.

In addition, when the percentage of cellulose gum, guar gum or acrylic polymer is increased, a product is obtained which exhibits mediocre initial foaming or which is difficult to remove by rinsing, because of the presence of a film-forming deposit on the skin which imparts a sensation of poorly cleansed skin. A need, therefore, continues to exist for foaming cleansing products of improved skin cleansing properties.

SUMMARY OF THE INVENTION

Accordingly, one object of the present invention is to provide foaming cleansing products which are rinsable and thick, but which nevertheless retain the properties required for foaming products, which are good miscibility with water, rapid transformation into a lather, good rinsing and good tolerability, in particular in the case of soap-containing foaming products.

Briefly, this object and other objects of the present invention as hereinafter will become more readily apparent can be attained by a cleansing composition comprising, in a physiologically acceptable aqueous medium comprising at least 35% by weight of water, relative to the total weight of the composition, (1) at least one foaming surfactant, (2) at least 1% by weight of at least one hydrophilic silica, relative to the total weight of the composition, and (3) at least one oxyalkylenated compound.

DETAILED DESCRIPTION OF THE PREFERRED EMBODIMENTS

It has now been discovered, surprisingly, that the combination of hydrophilic silica and of oxyalkylenated (oxyethylenated and/or oxypropylenated) compound makes it possible to obtain thick foaming cleansing products which do not run and which have a viscosity which is suitable for a creamy cleansing product. These products have a soft-solid and shear-thinning nature. The expression "product with a soft-solid nature" means herein a product which is malleable, which does not flow under its own weight and which has a loss angle δ ranging from 2° C. to 45° C. and a complex modulus G* ranging from $10^2$ to $10^5$ Pa for frequencies ranging from 0.01 to 10 Hz, δ and G* being defined below.

Admittedly, it is known practice to use silica in cleansing or detergent compositions. Thus, for example, U.S. Pat. No. 5,880,076 discloses a liquid detergent composition which may contain silica. EP 0 550 281 and U.S. Pat. No. 5,389,279 disclose silica as a powder which may be incorporated into cleansing compositions. However, the silicas used alone in the soap-free foaming products do not efficiently thicken the compositions and give the desired rheology. Neither of the publications discloses a combination of hydrophilic silica and of an oxyalkylenated compound to thicken foaming products.

Thus, one aspect of the present application is a cleansing composition comprising, in a physiologically acceptable aqueous medium comprising at least 35% by weight of water, relative to the total weight of the composition, (1) at least one foaming surfactant, (2) at least 1% by weight of at least one hydrophilic silica, relative to the total weight of the composition, and (3) at least one oxyalkylenated compound.

The expression "physiologically acceptable medium" means herein a medium which is compatible with the skin, mucous membranes, the scalp, the eyes and/or the hair. Moreover, it is an aqueous medium, i.e. a medium comprising an amount of water of at least 35% by weight, preferably ranging from 35% to 95% by weight and better still from 40% to 90% by weight relative to the total weight of the composition.

The compositions of the invention are foaming and rinsable cleansing compositions, and they are in the form of a thick translucent gel and behave like a shear-thinning soft solid, that is to say, they have viscoelastic behavior, with a complex modulus value G* ranging from $10^2$ to $10^5$ Pa and a loss angle value δ ranging from 2° C. to 45 ° C. for frequencies ranging from $10^{-2}$ to 10 Hz.

G* and δ are the viscoelastic parameters used to measure the physical properties of viscoelastic fluids, as explained in "An Introduction to Rheology" by H. A. Barnes, J. F. Hutton, K. Walters, pages 46 to 54 (published by Elsevier—1989).

G* is the complex modulus and δ is the loss angle. G' and G" are the components of $\overline{G^*}$, G' and G" are, respectively, the storage modulus and i of iG" is the loss modulus and is equal to $(-1)^{1/2}$. The components G' and G" of the complex modulus are derived from the relationship between the oscillatory stress and the oscillatory strain.

The rheological measurements of G* and δ are generally conducted in a Haake RS150 rheometer, at a temperature of 25° C., with measuring bodies having cone-plate geometry, the diameter of the cone and the size of the plate being 60 mm and the angle of the cone being 2° C. and the gap between the cone and the plate being 0.1 mm.

To make dynamic measurements of viscoelasticity (oscillatory measurements), the linear viscoelastic region is first determined by subjecting the sample to oscillatory stresses of increasing amplitude and of constant frequency. The moduli are recorded as a function of the amplitude of stress or of the amplitude of strain, in order to determine the limits of the linear viscoelastic region. After having identified the linear viscoelastic region, dynamic measurements are made in the linear viscoelastic region for a constant strain value lying in the linear viscoelastic region and at variable frequency. The Haake RS150 rheometer can cover a range of frequencies varying from 0.01 to 10 Hz, i.e. 0.063 to 62.8 rad/sec.

The following relationships are derived from the values of the amplitude of stress $\tau_0$ and the amplitude of strain $\gamma_0$, and also from the loss angle δ:

$G = \tau_0/\gamma_0$ $G' = G^* \cdot \cos \delta$ $G'' = G^* \cdot \sin \delta$ $\overline{G^*} = G' + iG''$ As mentioned above, the modulus G* of the composition of the invention ranges from $10^2$ to $10^5$ Pa and δ ranges from 2° C. to 45° C. for a frequency ranging from $10^{-2}$ to 10 Hz.

Despite the large G* value of the compositions of the invention, the rate of initiation of foaming is not reduced and the foam qualities and rinsing qualities are maintained.

Hydrophilic Silicas

In the present application the term "hydrophilic silica" means both pure hydrophilic silicas and particles coated with hydrophilic silica.

The amount of hydrophilic silica(s) in the composition of the invention, whether the silica is pure silica or particles coated with hydrophilic silica, must be at least 1% by weight in order to achieve the objective of the invention, and it may range, for example, on an active material weight basis, from 1% to 15% by weight, preferably from 2% to 10% by weight and even better still from 2% to 6% by weight relative to the total weight of the composition.

The hydrophilic silicas which may be used in the composition of the invention include preferably amorphous silicas and they may be of pyrogenic origin or of precipitated origin. They may be in pulverulent form or in the form of an aqueous dispersion.

Pyrogenic silicas are obtained by continuous flame pyrolysis of silicon tetrachloride ($SiCl_4$) at 1,000° C. in the presence of hydrogen and oxygen.

Precipitated silicas are obtained by reacting an acid with solutions of alkali metal silicates, preferably sodium silicate.

One silica or a mixture of two or more silicas may be used in the composition of the invention.

According to one preferred embodiment of the invention, the hydrophilic silica is selected from silicas having a specific surface area ranging from 30 to 500 $m^2/g$, a number-average particle size ranging from 3 to 50 nm and a compacted density ranging from 40 to 200, preferably from 50 to 150 g/l. The silicas more particularly are the hydrophilic silicas described in Tables (1) and (2) below, and mixtures thereof.

TABLE 1

| Trade name | Aerosil 90 (product of Degussa-Huels) | Aerosil 130 (product of Degussa-Huels) | Aerosil 150 (product of Degussa-Huels) | Aerosil 200 (product of Degussa-Huels) |
|---|---|---|---|---|
| Method of production | Pyrogenation | Pyrogenation | Pyrogenation | Pyrogenation |
| BET surface area ($m^2/g$) | 90 ± 15 | 130 ± 25 | 150 ± 15 | 200 ± 15 |
| Average particle size (nm) | 20 | 16 | 14 | 12 |
| Compacted density (g/l) | about 80 | about 50 | about 50 | about 50 |
| Density of the silanol groups ($OH/m^2$) | 2-3 | 2-3 | 2-3 | 2-3 |
| pH at 4% in water | 3.6-4.5 | 3.6-4.5 | 3.6-4.3 | 3.6-4.3 |
| Comment | | | | size of the aggregates: 10-30 and 200 μm |

TABLE 2

| Trade name | Aerosil 300 (product of Degussa-Huels) | Aerosil 380 (product of Degussa-Huels) | Aerosil OX 50 (product of Degussa-Huels) | Silice FK 320 DS (product of Degussa-Huels) |
|---|---|---|---|---|
| Method of production | Pyrogenation | Pyrogenation | Pyrogenation | Precipitation |
| BET surface area ($m^2/g$) | 300 ± 30 | 380 ± 30 | 50 ± 25 | 170 ± 25 |
| Average particle size (nm) | 7 | 7 | 40 | 18 |
| Compacted density (g/l) | about 50 | about 50 | about 130 | about 80 |
| Density of the silanol groups ($OH/m^2$) | 2-3 | 2-3 | 2-3 | — |
| pH at 4% in water | 3.6-4.5 | 3.6-4.5 | 3.8-4.5 | 6.3 |

It is also possible to use silica formulated in an aqueous dispersion, for example, a dispersion of colloidal silica, such as the product sold under the name Bindzil 30/220® by the company Eka Chemicals. This product is a colloidal dispersion of amorphous silica (size: 14 nanometers) in water (30/70).

The hydrophilic silica used in the composition of the invention may also be a particulate silica in which the particles are totally or partially coated with silica, in particular a mineral particle totally or partially coated with silica, such as the silica beads containing titanium oxide that are sold under the name Torayceram S-IT® by the company Toray; the silica-alumina microspheres containing titanium oxide (size: 105μ sold under the name Z-Light-Sphere W 1012® by the company Zeelan; the amorphous precipitated synthetic silica/titanium oxide particles (size: 106-500μ) sold under the name Neosil PC20S® by the company Crossfield; the Nylon-6-silica-titanium oxide fibers (length: 2 mm, and thickness: 2 denier) sold under the name Fiberlon Y2® by the company Wacker; the silica coated with titanium dioxide and covered with porous silica (85/5/10) (size: 0.6μ) sold under the name ACS-0050510® by the company SACI-CFPA; the anatase nanotitanium oxide treated with alumina and silica at 40% in water (size: 60 nm, monodisperse) sold under the name Mirasun TIW 60® by the company Rhodia Chimie CRA; the anatase nanotitanium oxide (60 nm) coated with silica/alumina/cerium IV 15/5/3 as an aqueous 32% dispersion, sold under the name Mirasun TIW 160® by the company Rhodia Chimie CRA; the anatase nanotitanium oxide treated with alumina and silica (34/4.3/1.7) as an aqueous 40% dispersion, sold under the name Tioveil AQ-N® by the company Uniqema; the nanotitanium oxide coated with silica (66/33) (titanium dioxide particle size: 30 nm; silica thickness: 4 nm), sold under the name Maxlight TS-04® by the company Nichimen Europe PLC; and the nanotitanium oxide coated with silica (80/20) (titanium dioxide particle size: 30 nm; silica thickness: 2 nm) sold under the name Maxlight TS-042® by the company Nichimen Europe PLC.

These particles may also have optical properties in the product and on the skin. For example, they may impart a matt effect or a slightly whitening effect.

Pyrogenic silicas and in particular in those sold under the names Aerosil 200® and Aerosil 300® by the company Degussa-Hüls are preferably used as the hydrophilic silica.

Oxyalkylenated Compounds

The oxyalkylenated compound(s) which may be used in the composition of the invention may comprise ethylene oxide groups (oxyethylenated compounds), propylene oxide groups (oxypropylenated compounds) or both (oxyethylenated/oxypropylenated compounds).

One or more oxyalkylenated compounds may be incorporated in the composition in an amount ranging, for example, on an active material weight basis, from 1% to 20% by weight, preferably from 2% to 10% by weight relative to the total weight of the composition.

Suitable oxyalkylenated compounds may be selected in particular from polyethylene glycols, polyethylene glycol esters and/or polypropylene glycol esters, polyethylene glycol ethers and/or polypropylene glycol ethers, alkoxylated acyl derivatives and in particular ethoxylated acyl polyol derivatives, oxyalkylenated and in particular oxyethylenated triesters of glycerol and of fatty acids, ethoxyethylenated urethane derivatives modified with alkyl chains, and mixtures thereof.

1. The polyethylene glycols which may be used in the composition of the invention include ethylene oxide polycondensates having a number of ethylene oxide (EO) units of greater than 10. The ethylene oxide number may range, for example, from 10 to 50,000 and preferably from 14 to 10,000. Suitable examples of polyethylene glycols include polyethylene glycol comprising 7,000 EO (CTFA name: PEG-7M), for instance the product sold under the name Polyox WSR N-750® by the company Amerchol, polyethylene glycol comprising 75 EO (CTFA name: PEG-75), polyethylene glycol comprising 20,000 EO (CTFA name: PEG-20M), for instance the product sold under the name Polyox WSR 1105® by the company Amerchol, and polyethylene glycol comprising 150 EO (CTFA name: PEG-150).

2. The polyethylene glycol esters and/or polypropylene glycol esters are condensates of polyethylene glycol and/or polypropylene glycol with one or more fatty acids. These compounds have the formula:

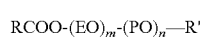

RCOO-(EO)$_m$-(PO)$_n$—R' in which $0 \leq m \leq 300$ and $0 \leq n \leq 300$ and $m+n \geq 6$, R and R' represent, independently of each other, hydrogen or a saturated or unsaturated, linear or branched, hydroxylated or non-hydroxylated alkyl chain containing from 1 to 30 carbon atoms, preferably from 12 to 22 carbon atoms, or an aryl chain, with the proviso that R and R' are not simultaneously hydrogen.

Suitable examples of polyethylene glycol acid esters and/or polypropylene glycol acid esters include polyethylene glycol distearate (150 EO), such as the product sold under the name Atlas G-1821® by the company Uniqema, PEG-150 dibehenate, such as the product sold under the name Ethox PEG 6000 Dibehenate® by the company Ethox, polyethylene glycol palmitostearate (120 EO), such as the product sold under the name Stearate 6000 WL 1644® by the company Gattefosse, the copolymer of polyethylene glycol (30 EO) and of 12-hydroxystearic acid, such as the product sold under the name Arlacel P135® by the company Uniqema, and polyethylene glycol stearate (40 EO), such as the product sold under the name MYRJ 52® by the company Uniqema.

In the case where R=R'=H, mention may be made, for example, of the polyoxyethylene polyoxypropylene statistic copolymer (17 EO /6 PO) sold under the name UCON 75-H-450® by the company AMERCHOL. Molecules having more EO and/or more PO are not excluded.

3. The polyethylene glycol ethers and/or polypropylene glycol ethers are condensates of polyethylene glycol and/or polypropylene glycol with one or more fatty alcohols. These compounds have the formula:

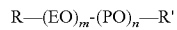

R—(EO)$_m$-(PO)$_n$—R' in which $0 \leq m \leq 300$ and $0 \leq n \leq 300$ and $m+n \geq 6$, R and R' represent, independently of each other, hydrogen or a saturated or unsaturated, linear or branched, hydroxylated or non-hydroxylated alkyl chain containing from 1 to 30 carbon atoms, preferably from 12 to 22 carbon atoms, or an aryl chain, with the proviso that R and R' are not simultaneously hydrogen.

Suitable examples of polyethylene glycol ethers include oxyethylenated (30 EO) cetyl alcohol, such as the product sold under the name Nikkol BC-30TX t® by the company Nikkol, oxyethylenated (15 EO) oleyl alcohol, such as the product sold under the name Nikkol BO-15TX® by the company Nikkol, oxyethylenated (50 EO) oleyl alcohol, such as the product sold under the name Nikkol BO-50® by the company Nikkol, oxyethylenated (10 EO) behenyl alcohol, such as the product sold under the name Mergital B 10® by the company Nikkol, oxyethylenated (30 EO) behenyl alcohol, such as the product sold under the name Nikkol BB-30® by the company Nikkol, oxyethylenated (12 EO) lauryl alcohol, such as the product sold under the name Rewopal 12® by the company Goldschmidt, oxyethylenated (23 EO) lauryl alcohol, such as the product sold under the name Simulsol P 23® by the company SEPPIC, oxyethylenated (20 EO) 2-octyldodecyl alcohol, such as the product sold under the name Octyldodeceth-20® by the company Stearinerie Dubois, oxyethylenated (20 EO) isocetyl alcohol, such as the product sold under the name Arlasolve 200 US@ by the company Uniqema, oxyethylenated (10 EO) oleyl alcohol, such as the product sold under the name Brij 97® by the company Uniqema, oxyethylenated (20 EO) oleyl alcohol, such as the product sold under the name Brij 98® by the company Uniqema, oxyethylenated (100 EO) stearyl alcohol, such as the product sold under the name Brij 700® by the company Uniqema, and oxyethylenated (21 EO) stearyl alcohol, such as the product sold under the name Brij 721® by the company Uniqema.

Suitable examples of polyethylene glycol/polypropylene glycol ethers, in particular, include oxyethylenated (5 EO) oxypropylenated (5 PO) lauryl alcohol, such as the product sold under the name Aethoxal B® by the company Cognis, oxypropylenated (3 PO) myristyl alcohol, such as the product sold under the name Promyristyl PM-3® by the company Croda, oxyethylenated (20 EO) oxypropylenated (5 PO) cetyl alcohol, such as the product sold under the name Procetyl AWS® by the company Croda, oxyethylenated (26 EO) oxypropylenated (26 PO) butyl alcohol, such as the product sold under the name PPG-26-Buteth-26® by the company Goldschmidt, oxyethylenated (26 EO) oxypropylenated (26 PO) butyl alcohol, such as the product sold under the name Varonic Apeb® by the company Goldschmidt, oxyethylenated (30 EO) oxypropylenated (6 PO) decyltetradecanol, such as the product sold under the name Nikkol PEN-4630® by the company Nikkol, and oxyethylenated (25 EO) oxypropylenated (25 PO) lauryl alcohol, such as the product sold under the name ADF-Oleile® by the company Vevy.

4. The ethoxylated alkyl or aryl derivatives of polyol may be, for example, oxyethylenated derivatives of fatty acid esters or of fatty alcohol ethers and of a polyol such as glycerol, sorbitol, glucose or pentaerythritol. Suitable derivatives of this type include, for example, oxyethylenated (78 EO) glyceryl cocoate, such as the product sold under the name Simulsol CG by the company SEPPIC, oxyethylenated (120 EO) methylglucose dioleate, such as the product sold under the name Glucamate DOE-120 Vegetal® by the company Amerchol, oxyethylenated (40 EO) sorbitan septaoleate, such as the product sold under the name Arlatone T® by the company Uniqema, oxyethylenated (10 EO) polyglyceryl (2 mol of glycerol) laurate, such as the product sold under the name HOE S 3495® by the company Clariant, oxyethylenated (60 EO) glyceryl isostearate, such as the product sold under the name Emalex GWIS-160® by the company SACI-CFPA, oxyethylenated (20 EO) glyceryl monostearate, such as the product sold under the name Cutina E 24® by the company Cognis, oxyethylenated (200 EO) glyceryl stearate, such as the product sold under the name Simulsol 220 TM@ by the company SEPPIC, and oxyethylenated (150 EO) pentaerythrityl tetrastearate, such as the product sold under the name Crothix® by the company Croda.

5. Oxyalkylenated glyceryl triesters of fatty acids include, for example, oxyethylenated (6 EO) caprylic/capric acid glycerides, such as the product sold under the name Softigen 767® by the company Condea, and oxyethylenated (50 EO) olive oil, such as the product sold under the name Crovol O-70® by the company Croda.

6. Ethoxyethylenated urethane derivatives modified with alkyl chains include, for example, those of formula (1) and (2):

in which the radicals $R_1$, $R_2$ and $R_3$ represent a $C_{1-18}$ alkyl group; $R_3$ and $R_6$ represent a linear, cyclic or aromatic $C_{4-36}$ hydrocarbon-based radical; $R_4$ represents a hydrogen atom or a $C_{1-6}$ alkyl radical, preferably a hydrogen atom; a is an integer ranging from 90 to 600 and b is an integer ranging from 1 to 4.

These derivatives include, for example, water-soluble polymers prepared by the addition reaction of a diisocyanate such as HMDI (hexamethylene diisocyanate) with a diol such as a polyether or a polyester, with the polymer ending with hydrophobic groups obtained from ethoxylated or ethoxylated/propoxylated fatty alcohols. This is the case, for example, for SER AD FX 1100 sold by the company Adriss, which is an oxyethylenated (100 BO) stearyl alcohol/polyethylene glycol (136 EO)/hexamethylene duisocyanate copolymer.

Suitable polymers of this type include, for example, the products sold under the names Acrysol 44 (or Aculyn 44) and Acrysol 46 (or Aculyn 46) (CTFA name: PEG-150/Decyl alcohol/SMDI Copolymer), which are polyurethanes obtained by condensation of hexamethylene diisocyanate and of polyethylene glycol, bearing a methyl residue and an octadecyl residue at their termini, respectively. These polyurethanes also contain from 3% to 5% of an enzymatically modified starch matrix. The polyurethanes are sold by the company Rohm & Haas. They are also the products Rheolate® 205, 210, 212, 216, 244, 278, 255, 266, 288, 300 and 350 sold by the company Elementis or the products Borchigel LW.44, L.75.N; L 76; VP 9628-LL36; VP 97105-NT40; VP 9620 sold by the company Borchers.

Surfactants

The foaming composition of the invention contains at least one surfactant which imparts a foaming characteristic to the composition. This surfactant may be selected from any nonionic, anionic, amphoteric or zwitterionic foaming surfactant and mixtures thereof.

The amount of surfactant(s) may range, for example, on an active material weight basis, from 2% to 50% by weight, preferably from 3% to 30% by weight relative to the total weight of the composition.

1. The nonionic surfactants:

Suitable nonionic surfactants which may be used, for example, include alkyl polyglucosides (APGs), maltose esters, polyglycerolated fatty alcohols, glucamine derivatives such as 2-ethylhexyloxycarbonyl-N-methylglucamine, and mixtures thereof.

Alkyl polyglucosides which are preferably used are those containing an alkyl group containing from 6 to 30 carbon atoms, preferably from 8 to 16 carbon atoms, and containing a hydrophilic group (glucoside) preferably comprising from 1.2 to 3 saccharide units. Suitable alkyl polyglucosides include, for example, decylglucoside (Alkyl C9/C11-poly-

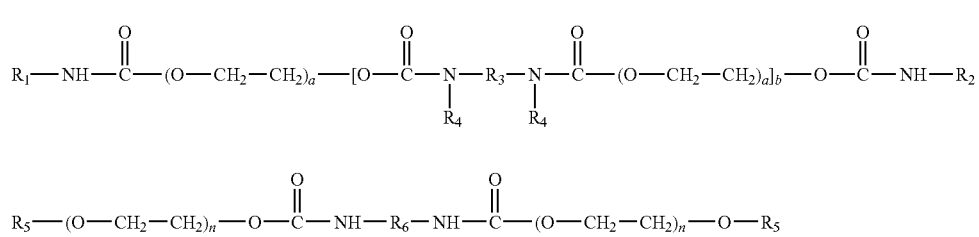

glucoside (1.4)), such as the product sold under the name Mydol 10® by the company Kao Chemicals, the product sold under the name Plantaren 2000 UPS by the company Henkel and the product sold under the name Oramix NS 10® by the company SEPPIC; caprylyl/capryl glucoside, such as the product sold under the name Oramix CG 110® by the company SEPPIC; laurylglucoside, such as the products sold under the names Plantaren 1200 N® and Plantacare 1200® by the company Henkel; and cocoglucoside, such as the product sold under the name Plantacare 818/UP® by the company Henkel.

The maltose derivatives include, for example, those disclosed in EP-A-566 438, such as O-octanoyl-6'-D-maltose or O-dodecanoyl-6'-D-maltose disclosed in FR-2 739 556.

Among the polyglycerolated fatty alcohols are polyglycerolated dodecanediol (3.5 mol of glycerol), this product being sold under the name Chimexane NF® by the company Chimex.

2. The anionic surfactants may be selected, in particular, from carboxylates, amino acid derivatives, alkyl sulfates, alkyl ether sulfates, sulfonates, isethionates, taurates, sulfosuccinates, alkyl sulfoacetates, phosphates and alkyl phosphates, polypeptides, anionic alkyl polyglucoside derivatives and fatty acid soaps, and mixtures thereof. Carboxylates include, for example, alkali metal salts of N-acylamino acids; amido ether carboxylates (AECs), for instance sodium lauryl amido ether carboxylate (3 EO) sold under the name Akypo Foam 30® by the company Kao Chemicals; polyoxyethylenated carboxylic acid salts, for instance oxyethylenated (6 EO) sodium lauryl ether carboxylate (C12-14-16 65/25/10) sold under the name Akypo Soft 45 NV® by the company Kao Chemicals; polyoxyethylenated fatty acids of olive oil and of carboxymethyl, this product being sold under the name Olivem 400® by the company Biologia E Technologia; oxyethylenated (6 EO) sodium tridecyl ether carboxylate sold under the name Nikkol ECTD-6NEX® by the company Nikkol.

The amino acid derivatives may be selected, for example, from sarcosinates and in particular acylsarcosinates, for instance the sodium lauroyl sarcosinate sold under the name Sarkosyl NL 97® by the company Ciba or sold under the name Oramix L 30® by the company SEPPIC, the sodium myristoyl sarcosinate sold under the name Nikkol Sarcosinate MN® by the company Nikkol or the sodium palmitoyl sarcosinate sold under the name Nikkol Sarcosinate PN® by the company Nikkol; alaninates, for instance the sodium N-lauroyl-N-methylamidopropionate sold under the name Sodium Nikkol Alaninate LN 30® by the company Nikkol or sold under the name Alanone ALE® by the company Kawaken, and the N-lauroyl-N-methylalanine triethanolamine sold under the name Alanone Alta® by the company Kawaken; N-acylglutamates, for instance the triethanolamine monococoylglutamate sold under the name Acylglutamate CT-12® by the company Ajinomoto and the triethanolamine lauroylglutamate sold under the name Acylglutamate LT-12® by the company Ajinomoto; aspartates, for instance the mixture of triethanolamine N-lauroyl aspartate and of triethanolamine N-myristoylaspartate, sold under the name Asparack® by the company Mitsubishi; citrates, and mixtures thereof.

Suitable alkyl ether sulfates include, for example, the sodium lauryl ether sulfate (C12-14 70/30) (2.2 EO) sold under the names Sipon AOS 225® or Texapon N702 PATE® by the company Henkel, the ammonium lauryl ether sulfate (C12-14 70/30) (3 EO) sold under the name Sipon Lea 370® by the company Henkel, and the ammonium (C12-C14) alkyl ether (9 EO) sulfate sold under the name Rhodapex AB/20® by the company Rhodia Chimie.

Suitable sulfonates include, for example, α-olefin sulfonates, for instance the sodium α-olefin sulfonate (C14-16) sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, the sodium secondary olefin sulfonate sold under the name Hostapur SAS 30® by the company Clariant; linear alkyl aryl sulfonates, for instance the sodium xylenesulfonate sold under the names Manrosol SXS30®, Manrosol SXS40® and Manrosol SXS93® by the company Manro.

Suitable isethionates include acylisethionates, for instance, sodium cocoylisethionate, such as the product sold under the name Jordapon CI P® by the company Jordan.

Suitable taurates include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant,or sold under the name Nikkol CMT-30-T® by the company Nikkol, and the sodium palmitoyl methyltaurate sold under the name Nikkol PMT® by the company Nikkol.

Suitable sulfosuccinates include, for example, the oxyethylenated (3 EO) lauryl monosulfosuccinate (C12/C14 70/30) sold under the names Setacin 103 Special, Rewopol SB-FA 30 K 4® by the company Witco, the disodium salt of a $C_{12}$-$C_{14}$-alkyl hemisulfosuccinate, sold under the name Setacin F Special Paste® by the company Zschimmer Schwarz, the oxyethylenated (2 EO) disodium oleamidosulfosuccinate sold under the name Standapol HS 135® by the company Henkel, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco.

Suitable phosphates and alkyl phosphates include, for example, monoalkyl phosphates and dialkyl phosphates, such as the lauryl monophosphate sold under the name MAP 20® by the company Kao Chemicals, the potassium salt of dodecylphosphoric acid, as a mixture of monoester and diester (mainly diester), sold under the name Crafol AP-31® by the company Cognis, the mixture of monoester and diester of octylphosphoric acid, sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium salt or triethanolamine salt of monoalkyl ($C_{12}$-$C_{13}$) phosphate sold under the references Arlatone MAP 230K-40® and Arlatone MAP 230T-60® by the company Uniqema, and the potassium lauryl phosphate sold under the name Dermalcare MAP XC-99/09® by the company Rhodia Chimie.

The polypeptides are prepared, for example, by coupling a fatty chain with amino acids from cereal grains, in particular from wheat and oat. Suitable polypeptides include, for example, the potassium salt of hydrolysed lauroyl wheat protein, sold under the name Aminofoam W OR® by the company Croda, the triethanolamine salt of hydrolysed cocoyl soybean protein, sold under the name May-Tein SYS by the company Maybrook, the sodium salt of oat lauroylamino acids, sold under the name Proteol Oat® by the company SEPPIC, the collagen hydrolysate grafted onto coconut fatty acid, sold under the name Geliderm 3000® by the company Deutsche Gelatine, and the soybean proteins acylated with hydrogenated coconut acids, sold under the name Proteol VS 22® by the company SEPPIC.

The anionic derivatives of alkylpolyglucosides may be, in particular, glyceryl ethers, carbonates, sulfosuccinates, tartrates and citrates obtained from alkyl polyglucosides. Suitable examples include the sodium salt of cocoylpolyglucoside (1,4) tartaric ester, sold under the name Eucarol AGE-ET® by the company Cesalpinia, the disodium salt of cocoylpolyglucoside (1,4) sulphosuccinic ester, sold under the name Essai 512 MP® by the company SEPPIC, and the sodium salt of cocoylpolyglucoside (1,4) citric ester, sold under the name Eucarol AGE-EC® by the company Cesalpinia.

Suitable fatty acid soaps include, as anionic surfactants, fatty acids of natural or synthetic origin, salified with a mineral or organic base. The fatty chain may comprise from 6 to 22 carbon atoms, preferably from 8 to 18 carbon atoms. The mineral or organic base may be selected from alkali metals or alkaline-earth metals, amino acids and amino alcohols. Suitable salts include, for example, the sodium, potassium, magnesium, triethanolamine and N-methylglucamine salts of lysine and of arginine. Suitable soaps include, for example, the potassium or sodium salts of lauric, myristic, palmitic or stearic acid (potassium or sodium laurate, myristate, palmitate and stearate), and mixtures thereof.

3. The amphoteric and zwitterionic surfactants may be selected, for example, from betaines, N-alkylamidobetaines and derivatives thereof, glycine derivatives, sultaines, alkyl polyaminocarboxylates and alkylamphoacetates, and mixtures thereof.

Suitable betaines include, for example, cocobetaine, for instance the product sold under the name Dehyton AB-30® by the company Henkel, laurylbetaine, for instance the product sold under the name Genagen KB® by the company Clariant, oxyethylenated (10 EO) laurylbetaine, for instance the product sold under the name Lauryl Ether (10 EO) Betaine® by the company Shin Nihon Rica, and oxyethylenated (10 EO) stearylbetaine, for instance the product sold under the name Stearyl Ether (10 EO) Betaine® by the company Shin Nihon Rica.

Suitable among the N-alkylamidobetaines and derivatives thereof, for example, are the cocamidopropylbetaines sold under the name Lebon 2000 HG® by the company Sanyo, or sold under the name Empigen BB® by the company Albright & Wilson, and the lauramidopropyl betaine sold under the name Rewoteric AMB12P® by the company Witco.

Suitable glycine derivatives include the sodium N-cocoylglycinate sold under the name Amilite GCS-12® by the company Ajinomoto.

Suitable sultaines which may be mentioned include the cocoylamidopropylhydroxysulfobetaine sold under the name Crosultaine C-50 by the company Croda.

Suitable alkyl polyaminocarboxylates (APACs) include the sodium cocoylpolyaminocarboxylate sold under the name Ampholak 7 CX/C® and Ampholak 7 CX® by the company Akzo Nobel, the sodium stearylpolyamidocarboxylate sold under the name Ampholak 7 TX/C by the company Akzo Nobel and the sodium carboxymethyloleylpolypropylamine sold under the name Ampholak X07/C® by the company Akzo Nobel.

Suitable alkylamphoacetates include, for example, N-disodium N-cocoyl-N-carboxymethoxyethyl-N-carboxymethylethylenediamine (CTFA name: disodium cocamphodiacetate), for instance the product sold under the name Miranol C2M Concentre NP® by the company Rhodia Chimie and N-sodium N-cocoyl-N-hydroxyethyl-N-carboxymethylethylenediamine (CTFA name: sodium cocamphoacetate).

According to one particular embodiment of the invention, among the surfactants mentioned above, the anionic surfactants more particularly useful are acylsarcosinates, oxyethylenated alkyl ether sulfates, N-acyl N-methyltaurates, N-acylglutamates, acylisethionates, sulfosuccinates, phosphates and alkyl phosphates, polypeptides and soaps; the amphoteric and zwitterionic surfactants more particularly useful are betaines and alkylamphoacetates; the nonionic surfactants more particularly useful are alkyl polyglucosides, O-octanoyl-6'-D-maltose, O-dodecanoyl-6'-D-maltose, polyglycerolated dodecanediol (3.5 mole of glycerol) and 2-ethylhexyloxycarbonyl N-methylglucamine; and mixtures of these surfactants.

The aqueous medium of the composition of the invention may contain, in addition to water, one or more solvents selected from lower alcohols containing from 1 to 6 carbon atoms, such as ethanol; and polyols. Suitable polyols include glycerol; glycols, for instance, butylene glycol, isoprene glycol, propylene glycol and polyethylene glycols such as PEG-8; sorbitol; sugars such as glucose, fructose, maltose, lactose or sucrose; and mixtures thereof. The amount of solvent(s) in the composition of the invention may range, for example, from 0.5% to 30% by weight and preferably from 2% to 20% by weight relative to the total weight of the composition.

The compositions of the invention have a viscosity preferably ranging from 25 poises (2.5 Pa·s) to 700 poises (70 Pa·s) and more particularly from 50 poises (5 Pa·s) to 300 poises (30 Pa.s), these viscosities being measured using a Rheomat Mettler RM 180 machine at 25° C., this machine being fitted with a different spindle depending on the viscosities, for example a No. 2 spindle for viscosity ranges of less than 7 poises, a No. 3 spindle for viscosity ranges from 2 to 40 poises and a No. 4 spindle for viscosity ranges from 20 poises to 80 poises.

The compositions of the invention may contain adjuvants normally employed in cosmetics, and in particular those used in cleansing products. Suitable adjuvants include, for example, fragrances, preserving agents, sequestering agents (EDTA), pigments, nacres, mineral or organic fillers, matt-effect agents, bleaching or exfoliant agents, soluble colorants, sunscreens, cosmetic or dermatological active agents such as water-soluble or liposoluble vitamins, antiseptics, antiseborrhoeic agents, antimicrobial agents such as benzoyl peroxide, salicylic acid, triclosan and azelaic acid, and also sold by the company CLAREMONT FLOCK CORPORATION).

The compositions of the invention may in particular constitute cleansing or make-up-removing products for the skin (body, face and eyes), the scalp and/or the hair.

Another aspect of the invention is the cosmetic use of the composition as defined above, as a product for cleansing and/or for removing make-up from the skin, the eyes, the scalp and/or the hair.

The compositions of the invention may also constitute compositions for treating greasy skin and/or for disinfecting the skin and/or the scalp, in particular when they contain an antibacterial agent. In particular, specific active agents for treating greasy skin may be included therein, such as, for example, salicylic acid, azelaic acid, triclosan, piroctone olamine or niacinamide (vitamin PP).

Another aspect of the invention is the use of the composition as defined above for the preparation of a composition intended for treating greasy skin and/or for disinfecting the skin and/or the scalp.

Still another aspect of the invention is a process for cleansing the skin, the eyes, the scalp and/or the hair, in which the composition of the invention is applied to the skin, the eyes, the scalp and/or the hair, in the presence of water, and the lather formed and the soiling residues are removed by rinsing with water.

In the case of cleansing the face, the composition according to the invention may constitute a mask which is removed by rinsing after it has been left on for a period of 1 to 3 minutes.

The examples which follow serve to illustrate the invention without, however, being limiting in nature. The amounts indicated are percentages by weight, except where otherwise mentioned.

Table 3 below shows an example of the invention (soap-free foaming composition) and comparative examples. The rheological properties were obtained using a Haake R S150 rheometer, at 25° C.

TABLE 3

| Composition | Comparative Ex. 1 | Comparative Ex. 2 | Comparative Ex. 3 | Ex. 1 according to the invention |
|---|---|---|---|---|
| Cocobetaine [Dehyton AB-30 ® at 30% active material (A.M.)] | 0 | 9.75% (A.M.) | 9.75% (A.M.) | 9.75% (A.M.) |
| Sodium laureth sulphate [Texapon N702 Paste ® at 70% active material (A.M.)] | 0 | 2.6% (A.M.) | 2.6% (A.M.) | 2.6% (A.M.) |
| PEG-120 methyl-glucose dioleate (Glucamate DOE12) | 4% | 0 | 4% | 4% |
| Hydrophilic silica (Aerosil 200 ®) | 5% | 5% | 0 | 5% |
| Sorbitol | 3.5% | 3.5% | 3.5% | 3.5% |
| Glycerol | 3.5% | 3.5% | 3.5% | 3.5% |
| Preserving agents | qs | qs | qs | qs |
| Water | qs 100 g | qs 100 g | qs 100 g | qs 100 g |
| Appearance | Liquid product like water (viscosity from 1 to 100 cPoises) | Translucent liquid product like water (viscosity from 1 to 100 cPoises) | Runny crystalline gel | Thick translucent gel |
| pH | 6.6 | 6.7 | 7 | 6.2 |
| Viscosity under shear at 1000 s$^{-1}$ at approximately 25° C. | | 0.35 Pa·s | 0.0185 Pa·s | 0.032 Pa·s |
| Rheological properties | | | | |
| −G*)Pa) to 10$^{-2}$ Hz | | 0.01 | 0.16 | 564 |
| =G*)Pa) to 1 Hz | | 0.6 | 17 | 958 |
| −δ (deg.) to 10$^{-2}$ Hz | | 88 | 90 | 11 |
| −δ (Deg.) to 1 Hz | | 90 | 89 | 23 |

Thus, only the example of the invention which comprises a foaming surfactant and hydrophilic silica (Aerosil 200) combined with an oxyethylenated compound (PEG-120 methyl-glucose dioleate) has the desired "soft-solid" type of behavior, with δ ranging from 2 to 45° C., for stresses whose frequencies range from 10-z to 1 Hz. The viscosity values at 1000 s$^{-1}$ show that the composition of the invention and the compositions of the comparative examples behave similarly under shear, whereas they behave differently at rest. The composition of the invention has a thick consistency at rest (Example 1), which is not the case for the compositions of the comparative examples, which are liquid (Comparative Examples 1 and 2) or runny (Comparative Example 3). This clearly shows the behavior of "soft solid" and shear-thinning types of compositions of the invention. Because of the fact that it is thick at rest, the composition of the invention has the advantage of being easier to take-up and to apply.

Sensory performance qualities: the developed foam qualities are evaluated according to the protocol described below.

Before any use of the products, the hands are washed with household soap and then suitably rinsed and dried. The protocol followed is then as follows:

1—wet the hands by passing them under running water, and shake them three times to drain the water off,
2—place 1 g of product in the palm of one of the hands,
3—work the product between the two palms for 10 seconds,
4—add 2 ml of water and work the product again for 10 seconds,
5—rinse the hands under water,
6—dry them.

The criteria are evaluated at each step of the protocol followed, and they are graded on a scale from 0 to 10.

Step 3: evaluation of the covering power: the grade attributed is proportionately higher the less the skin can be seen through the product spread on.

Step 4: evaluation of the foam quality

The foam volume: the grade given is proportionately higher the greater the volume.

The size of the bubbles of which the foam is formed: the grade given is proportionately higher the larger the bubbles.

The density: foam consistency and behavior: the grade given is proportionately higher the greater the density.

The foam softness: the grade given is proportionately higher the softer the foam.

Step 5: evaluation during rinsing

The rinsing: the grade given is proportionately lower the greater the presence of a slippery film which is difficult to remove.

The sensory results for each of the criteria are as follows:

| | Comparative Ex. 3 | Ex. 1 of the invention |
|---|---|---|
| Speed of appearance of the first bubbles | 10 | 9.8 |
| Covering power | 6.3 | 6.4 |
| Foam volume | 6.4 | 6.6 |
| Size of the bubbles | 4.5 | 4.8 |
| Density | 6.9 | 7.8 |
| Foam softness | 6.4 | 6.1 |
| Rinsing | 6.9 | 7.1 |

The difference between the two values must be greater than or equal to 1 to be significant.

Thus, the addition of hydrophilic silica and of oxyethylenated compound does not modify the speed of appearance of the first bubbles, despite the greatly modified rheology of the composition of the invention relative to the control.

EXAMPLE 2

Soap-free foaming composition

| | |
|---|---|
| Lauryl monophosphate (containing 75% monoester) (MAP 20 ®) | 6.5% (in A.M.) |
| Alkyl-C9/C11-polyglucoside (1.4) (Mydol 10) | 6.5% (in A.M.) |
| Potassium hydroxide | 1.7% |

|  |  |
|---|---|
| PEG-120 methylglucose dioleate (Glucamate DOE-120 Vegetal ®) | 2% |
| Hydrophilic silica (Aerosil 200 ®) | 5% |
| Preserving agents | qs |
| Water | qs 100% |

A non-runny thick gel of pH 7.1 is obtained, which foams well, giving a soft, fine foam. This gel has a viscosity under shear at 1000 s$^{-1}$ of 0.06 and the following rheological properties

|  |  |
|---|---|
| –G* (Pa) to 10$^{-2}$ Hz | 2170 |
| –G* (Pa) to 1 Hz | 2670 |
| –δ (deg.) to 10$^{-2}$ Hz | 6 |
| –δ (deg.) to 1 Hz | 17 |

EXAMPLE 3

Foaming composition containing soaps

|  |  |
|---|---|
| Potassium laurate | 2% |
| Potassium myristate | 3.3% |
| Potassium palmitate | 2.3% |
| Potassium stearate | 3.7% |
| PEG-180 | 2% |
| Aerosil 200 ® | 3% |
| Sorbitol | 3.5% |
| Glycerol | 3.5% |
| Butylene glycol | 6% |
| Preserving agents | qs |
| Water | qs 100 |

The composition is in the form of a thick translucent product of pH 9, has the appearance of a cream and gives a fine, soft foam.

The disclosure of French priority application Serial Number 0009225 filed Jul. 13, 2000 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A cleansing composition, comprising:
(1) at least one foaming surfactant, (2) at least 1% by weight of at least one hydrophilic silica, relative to the total weight of the composition, and (3) at least one oxyethylenated ester, optionally comprising oxypropylenated groups, in a physiologically acceptable aqueous medium comprising at least 35% by weight of water, relative to the total weight of the composition.

2. The composition according to claim 1, which has a complex modulus G* ranging from 102 to 105 Pa and a loss angle ranging from 2° C. to 45° C. for frequencies ranging from 0.01 to 10 Hz.

3. The composition according to claim 1, which comprises from 35% to 95% by weight of water relative to the total weight of the composition.

4. The composition according to claim 1, wherein the amount of hydrophilic silica(s) ranges from 1% to 15% on an active material weight basis relative to the total weight of the composition.

5. The composition according to claim 1, wherein the hydrophilic silica is selected from the group consisting of silicas of pyrogenic origin, of precipitated origin, and mixtures thereof.

6. The composition according to claim 1, wherein the hydrophilic silica is selected from the group consisting of silicas having a specific surface ranging from 30 to 500 m$^2$/g, a number-average particle size ranging from 3 to 50 nm and a compacted density ranging from 40 to 200 g/l.

7. The composition according to claim 1, wherein the hydrophilic silica is a pyrogenic silica.

8. The composition according to claim 7, wherein the hydrophilic silica consists of a particle coated with hydrophilic silica.

9. The composition according to claim 1, wherein the amount of oxyalkylenated ester(s) ranges from 1% to 20% on an active material weight basis relative to the total weight of the composition.

10. A composition according to claim 1, wherein the composition comprises at least one oxyethylenated ester of the formula:

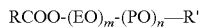

wherein 0<m≦300 and 0≦n≦300 and m+n≧6, R and R' represent, independently of each other, hydrogen or a saturated or unsaturated, linear or branched, hydroxylated or non-hydroxylated alkyl chain containing from 1 to 30 carbon atoms, or an aryl chain, with the proviso that R and R' are not simultaneously hydrogen.

11. A composition according to claim 1, wherein the composition comprises at least one oxyethylenated ester of a polyol and of a fatty acid.

12. The composition according to claim 1, wherein the foaming surfactant is selected from the group consisting of nonionic surfactants, anionic surfactants, amphoteric surfactants, zwitterionic surfactants, and mixtures thereof.

13. The composition according to claim 1, wherein the amount of foaming surfactant(s) ranges from 2% to 50% on an active material weight basis relative to the total weight of the composition.

14. The composition according to claim 10, wherein the foaming surfactant is selected from the group consisting of alkyl polyglucosides, maltose esters, polyglycerolated fatty alcohols, glucamine derivatives, carboxylates, amino acid derivatives, alkyl sulfates, alkyl ether sulfates, sulfonates, isethionates, taurates, sulfosuccinates, alkyl sulfoacetates, phosphates and alkyl phosphates, polypeptides, anionic alkyl polyglucoside derivatives, fatty acid soaps, betaines, N-alkylamidobetaines and derivatives thereog glycine derivatives, sultaines, alkyl polyaminocarboxylates, alkylamphoacetates, and mixtures thereof.

15. The composition according to claim 1, which further comprises at least one solvent selected from the group consisting of alcohols comprising from 1 to 6 carbon atoms, polyols and mixtures thereof.

16. A method of cleansing and/or removing makeup from the skin, the eyes, the scalp and/or the hair, comprising:

applying the composition of claim 1 to the skin, the eyes, the scalp and/or the hair thereby cleansing and/or removing make-up from the skin, the eyes, the scalp and/or the hair.

17. A method of treating greasy skin, comprising:
applying the composition of claim 1 to the skin, thereby removing grease from the skin.

18. A method of disinfecting the skin and/or the scalp, comprising:
applying the composition of claim 1 to the skin and/or the scalp, thereby disinfecting the skin and/or the scalp.

19. A method of cleansing the skin, the eyes, the scalp and/or the hair, comprising:
applying the composition of claim 1 to the skin, the eyes, the scalp and/or the hair in the presence of water thereby forming a lather; and
removing the lather containing soiling residues by rinsing the lather from the skin, the eyes, the scalp and/or the hair with water.

20. A cosmetic mask, comprising:
an applied composition of claim 1 as a mask on the skin of the face.

21. A composition according to claim 1, wherein the oxyethylenated ester does not contain oxypropylenated groups.

22. A composition according to claim 11, wherein the polyol is selected from the group consisting of glycerol, sorbitol, glucose and pentaerythritol.

23. A composition according to claim 22, wherein the polyol is glycerol, soritol or glucose.

* * * * *

UNITED STATES PATENT AND TRADEMARK OFFICE
CERTIFICATE OF CORRECTION

| | | |
|---|---|---|
| PATENT NO. | : 7,670,999 B2 | Page 1 of 1 |
| APPLICATION NO. | : 09/903785 | |
| DATED | : March 2, 2010 | |
| INVENTOR(S) | : Laurence Sebillotte-Arnaud et al. | |

It is certified that error appears in the above-identified patent and that said Letters Patent is hereby corrected as shown below:

Column 16, line 58, claim 14, "thereog" should read --thereof,--.

Signed and Sealed this

Eleventh Day of May, 2010

David J. Kappos
*Director of the United States Patent and Trademark Office*